(12) United States Patent
Edic et al.

(10) Patent No.: US 7,396,162 B1
(45) Date of Patent: Jul. 8, 2008

(54) SCATTER CORRECTION FOR CT METHOD AND APPARATUS

(75) Inventors: Peter Michael Edic, Albany, NY (US); Samit Kumar Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/731,357

(22) Filed: Mar. 30, 2007

(51) Int. Cl.
*G01D 18/00* (2006.01)

(52) U.S. Cl. .................................. 378/207; 378/7; 378/9

(58) Field of Classification Search ............... 378/4, 378/5, 6, 7, 9, 19, 207, 901
See application file for complete search history.

(56) References Cited

U.S. PATENT DOCUMENTS 7,334,940 B2 * 2/2008 Nukui ........................ 378/207

* cited by examiner

*Primary Examiner*—Courtney Thomas
(74) *Attorney, Agent, or Firm*—Fletcher Yoder

(57) ABSTRACT

A method, system, and machine readable media are provided for correcting scatter in an image. The method comprises sequentially emitting radiation from a subset of radiation sources toward a detector array and measuring radiation on areas of the detector array not exposed to the emitted primary radiation at the time of measurement. Scatter is estimated from the measured radiation. Furthermore, the scatter estimates are subtracted from the measured data and images with improved image quality are reconstructed.

25 Claims, 3 Drawing Sheets

SCATTER CORRECTION FOR CT METHOD AND APPARATUS

BACKGROUND

The present invention relates generally to the field of non-invasive imaging and more specifically to the field of computed tomography. In particular, the present invention relates to improving image quality by estimating and reducing scatter in an X-ray imaging system.

CT scanners operate by emitting fan-shaped or cone-shaped X-ray beams from an X-ray source towards a detector. The X-ray source emits X-rays at numerous angular positions relative to an object being imaged, such as a patient, which attenuates the X-ray beams as they traverse the object. The attenuated X-ray beams are detected by a set of detector elements, which produce signals representing the attenuation of the incident X-ray beams. The signals are processed to produce data corresponding to the line integrals of the attenuation coefficients of the object along X-ray paths connecting the source and detector elements. These signals are typically called "projection data" or just "projections". By using reconstruction techniques, such as filtered backprojection, useful images may be formulated from the projections. The images may in turn be associated to form a volume rendering of a region of interest. In a medical context, pathologies or other structures of interest may then be located or identified from the reconstructed images or rendered volume.

It is generally desirable to develop CT scanners with high spatial and temporal resolution, good image quality, and good coverage along the z-axis, i.e., the longitudinal or rotational axis of the CT scanner. To meet some or all of these objectives, it may be desirable to increase the coverage provided by the detector, thereby allowing greater scan coverage in one or more dimensions. For example, z-axis coverage of the detector may be lengthened by increasing the number of rows of detector elements in the detector.

However, various physical factors associated with the X-ray imaging process may lead to artifacts in the resulting images or to blurring or generally poor image quality. For example, X-rays photons emitted through the imaging volume may pass through the patient or other object being imaged or be absorbed by the patient or object and thus never reach the detector. The amounts of X-ray photons passing through the patient and the amount attenuated are useful to produce the desired radiographic images as this information is indicative of the composition and structure of the patient or object undergoing imaging. At operating voltages of typical X-ray systems, less than 1 megavolt, three dominate absorption processes contribute to the mass attenuation coefficient of the object: photoelectric absorption, Rayleigh scattering, and Compton scattering. Photoelectric absorption is a mechanism where the energy of the photon is absorbed by the material's electrons and liberated. Rayleigh scattering is an interaction between the photon and material's electrons, where the photon direction is slightly altered, without any loss of energy. Compton scatter is an interaction where the material absorbs part of the energy of the photon; however, the photon continues to traverse the object or patient along an altered direction. Unlike X-ray photons that are photo-electrically absorbed or undergo Rayleigh scattering, an X-ray photon that is attenuated by the Compton scattering mechanism may eventually reach the detector apparatus but typically along a different trajectory. As a result, a scattered X-ray photon may impact the detector at a location or from a direction that conveys no useful composition or structural information about the patient or object undergoing imaging. As a result, the scattered X-ray photons may lead to blur within the resulting radiographic image or otherwise reduce the image quality, such as CT number nonuniformity or a reduction in the contrast-to-noise ratio in a reconstructed image. The likelihood of such scattering may be increased in imaging systems employing multiple X-ray sources or emission points or increased coverage on the patient or object being imaged.

In order to reduce scatter, collimators or anti-scatter grids may be used, which are focally aligned to the X-ray beams from the sources to the detector elements, with a corresponding increase in mechanical complexity and cost of the overall CT system. Further, use of collimators with higher resolution detectors has proven challenging due to the small size of the detector elements or pixels. An alternative method of estimating scatter by attempting to extrapolate scatter signals from detector elements at opposing lateral sides of the detector array has proven difficult and does not provide a reliable estimate for scatter across the full axial volume. A technique for reducing scatter in X-ray imaging while reducing the mechanical complexity and cost of the imaging system is therefore desirable.

BRIEF DESCRIPTION

A method for correcting scatter in an image is provided. The method includes the act of emitting radiation from one or more sources of radiation towards a detector array and measuring radiation on areas of the detector array that are not exposed to the emitted primary radiation at the time of measurement. Scatter is estimated from the measured radiation. Corresponding claims to tangible, machine readable media comprising code executable to perform these acts are also provided.

An imaging system is provided. The imaging system includes one or more radiation sources along the z-axis configured to emit a beam of radiation. The imaging system also includes a detector array comprising a plurality of detector elements. The detector array may generate one or more signals in response to the respective beams of radiation. The imaging system also includes a system controller configured to control the radiation sources, including activating subsets of the radiation sources sequentially. In addition, the system controller is configured to acquire the one or more signals from the plurality of detector elements, including detector elements not exposed to the primary beams of radiation at the time of acquisition. The imaging system also includes a computer system configured to estimate scatter over the entire detector array.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
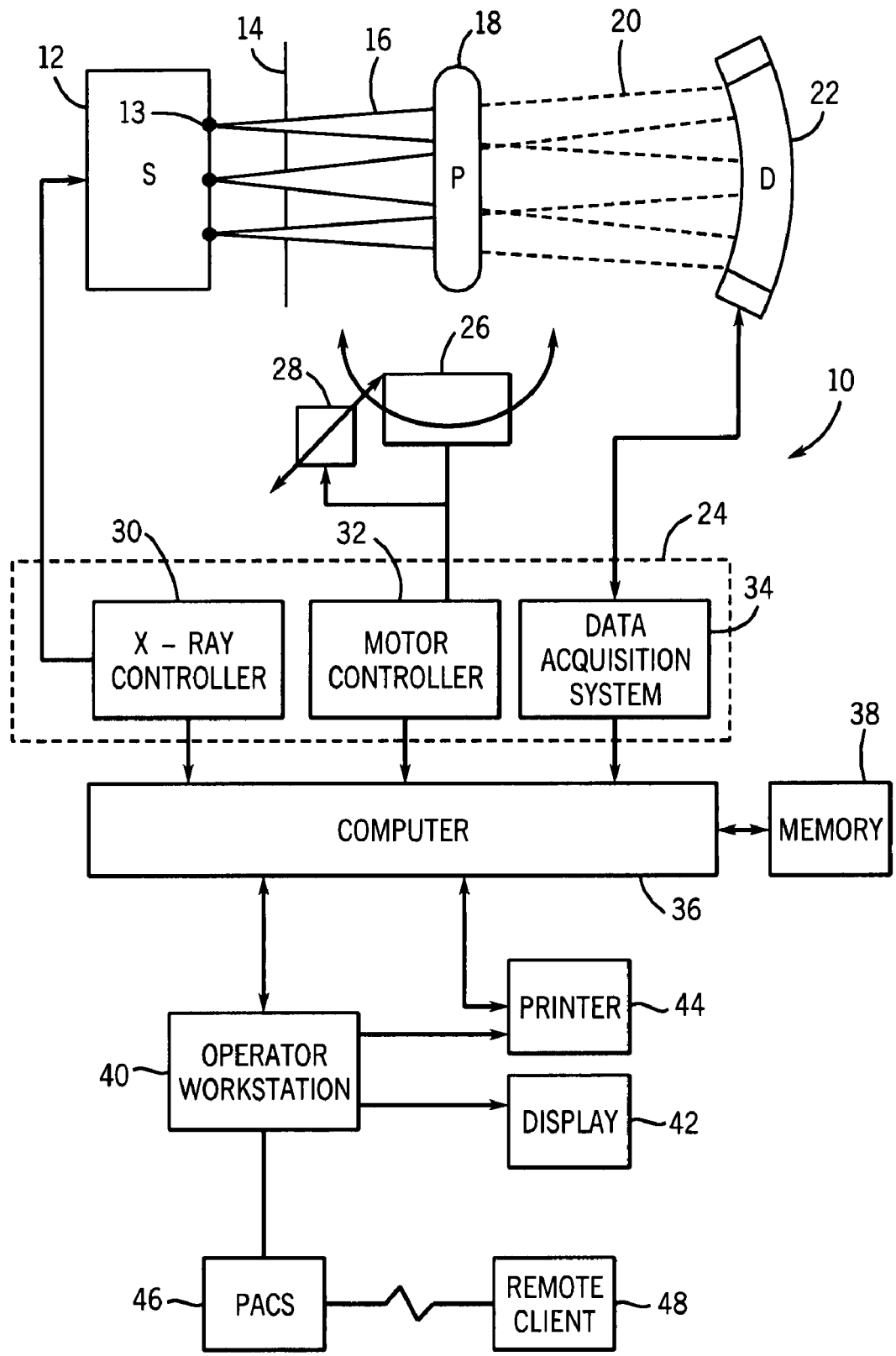
FIG. 1 is a diagrammatical view of an exemplary imaging system in the form of a CT imaging system for use in producing processed images, in accordance with one aspect of the present technique.

FIG. 1 illustrates diagrammatically an imaging system 10 for acquiring and processing image data. In the illustrated embodiment, system 10 is a computed tomography (CT) system designed to acquire X-ray projection data, to reconstruct the projection data into an image, and to process the image data for display and analysis in accordance with the present technique. Though the imaging system 10 is discussed in the context of medical imaging, the techniques and configurations discussed herein are applicable in other non-invasive CT imaging contexts, such as baggage or package screening. In the embodiment illustrated in FIG. 1, CT imaging system 10 includes a source 12 of X-ray radiation. As discussed in detail herein, the source 12 of X-ray radiation may be any source configured to emit X-rays from one or more z-locations or emission points 13. For example, the X-ray source 12 may consist of multiple X-ray tubes arranged at different locations along the z-axis. Similarly, the X-ray source 12 may include one or more addressable solid-state sources. Such solid-state sources may be configured as arrays of field emitters, including one-dimensional arrays, i.e., lines, and two-dimensional arrays. Although three emission points 13 are shown in FIG. 1, source 12 may include one or more emission points 13. Moreover, the emission points 13 are shown for illustration purposes only.

The X-ray source 12 may be positioned proximate to a collimator 14. The collimator 14 may consist of one or more collimating regions, such as lead or tungsten shutters, for each emission point of the source 12. The collimator 14 typically defines the size and shape of the one or more beams of radiation 16 that pass into a region in which a human patient 18 is positioned. A beam of radiation 16 may be generally fan or cone-shaped depending on the configuration of the detector array, as discussed below, as well as the desired method of data acquisition. An unattenuated portion of the radiation 20 passes through the subject, which provides the attenuation, and impacts a detector array, represented generally at reference numeral 22.

The detector 22 is generally formed by a plurality of detector elements, which detect the X-rays that pass through or around a subject of interest. Each detector element produces an electrical signal that represents the intensity of the X-ray beam at the position of the element during the time the beam strikes the detector. Typically, signals are acquired at a variety of angular positions around the subject of interest so that a plurality of radiographic views may be collected. These signals are acquired and processed to reconstruct an image of the features within the subject, as described below.

The X-ray source 12 is controlled by a system controller 24, which furnishes power, focal spot location, control signals and so forth for CT examination sequences. Moreover, the detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal-processing circuitry and associated memory circuitry. The associated memory circuitry may store programs and routines executed by the computer, configuration parameters, image data, and so forth. The system controller 24 may also be a general purpose or application-specific computer system.

In the embodiment illustrated in FIG. 1, system controller 24 may control the movement of a linear positioning subsystem 28 and rotational subsystem 26 via a motor controller 32. In imaging systems 10 in which the source 12 and/or the detector 22 may be rotated, the rotational subsystem 26 may rotate the X-ray source 12, the collimator 14, and/or the detector 22 through one or multiple turns around the patient 18. It should be noted that the rotational subsystem 26 might include a gantry. The linear positioning subsystem 28 enables the patient 18, or more specifically a patient table, to be displaced linearly. Thus, the patient table may be linearly moved within a gantry that includes a rotating source 12 and detector 22 or within a stationary source 12 and/or detector 22 configuration to generate images of particular areas of the patient 18. In embodiments comprising a stationary source 12 and a stationary detector 22, the rotational subsystem 26 may be absent. Similarly, in embodiments in which the source 12 and the detector 22 are configured to provide extended coverage along the z-axis, i.e, the axis associated with the main length of the patient 18, the linear positioning subsystem 28 may be absent.

As will be appreciated by those skilled in the art, the distributed source 12 of radiation may be controlled by an X-ray controller 30 disposed within the system controller 24. The X-ray controller 30 may be configured to provide power and timing signals to the X-ray source 12 or emission points 13 therein. In addition, the X-ray controller may be configured to selectively activate the distributed X-ray source 12 such that tubes or emission points at different locations along the z-axis may be activated individually or in subsets.

Further, the system controller 24 may comprise a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor-based system, such as a computer 36.

The computer 36 is typically coupled to or incorporates the system controller 24. The data collected by the data acquisition system 34 may be transmitted to the computer 36 for subsequent processing and reconstruction. For example, the data collected from the detector 22 may undergo pre-processing and calibration at the data acquisition system 34 and/or the computer 36 to process the data to represent the line integrals of the attenuation coefficients of the scanned objects. The processed data, commonly called projections, may then be filtered and backprojected to formulate an image of the scanned area. In one exemplary embodiment, the computer 36 uses data collected from the detector 22 to estimate scatter, such as due to Compton scattering, and then process the scatter signal. Before filtering and backprojection, the computer 36 may subtract the scatter estimate from intensity measurements prior to computing the projection data. Once reconstructed, the image produced by the system of FIG. 1 reveals an internal region of interest of the patient 18 which may be used for diagnosis, evaluation, and so forth. Alternately, the estimated scatter signals may be fed into an iterative reconstruction algorithm, which incorporates the scatter estimate into a forward model for the data acquisition, thereby implicitly correcting for the scatter in the data.

The computer 36 may comprise or communicate with a memory 38 that can store data processed by the computer 36 or data to be processed by the computer 36. It should be understood that any type of computer accessible memory device capable of storing the desired amount of data and/or code may be utilized by such an exemplary system 10. Moreover, the memory 38 may comprise one or more memory devices, such as magnetic or optical devices, of similar or different types, which may be local and/or remote to the system 10. The memory 38 may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 which may be equipped with a keyboard and/or other input devices. An operator may thereby control the system 10 via the operator workstation 40. Thus, the operator may observe the reconstructed image and other data relevant to the system from computer 36, initiate imaging, and so forth.

A display 42 coupled to the operator workstation 40 may be utilized to observe the reconstructed images. Additionally, the scanned image may be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image data.

One or more operator workstations 40 may be linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The CT imaging system 10 described above may be modified or configured in a variety of ways to improve spatial and temporal resolution, to improve image quality, and/or to improve z-axis coverage. Indeed, various source 12 and detector 22 configurations may be implemented which improve one or more of these parameters. In the example embodiment, the distributed X-ray source 12 includes two to fifteen emission points, such as X-ray tubes or field emitters, along the z-axis (typically the axis of rotation or the axis running through the bore of the scanner) to improve or increase z-axis coverage. As will be explained in FIGS. 2-4, the emission points are sequentially activated in interleaved subsets. The number of emission points in each subset may be determined by dividing the total number of emission points by any integer between two and the total number of emission points. In the exemplary embodiment depicted in FIGS. 2-4, each subset consists of one-third of the total number of emission points in the embodiment. The subsets of emission points are activated such that radiation beams 16 generated by the different emissions points do not concurrently impact the same detector elements of the detector 22. As a result, some areas on the detector array 22 will be outside the area exposed to the primary radiation beams. As used herein, the term primary radiation refers to radiation emitted from the emission points that would be incident on the detector array without undergoing any of the absorption or scatter processes described above. The only radiation received on those areas of the detector array outside the areas exposed to the primary radiation is scattered radiation, and the signals from these areas, when read by the data acquisition system 24, are used by the computer 36 to estimate scatter. After every subset of emission points has been activated, the scatter estimations can then be interpolated to provide a scatter estimate along the entire 2D array of detector elements.

Figure 2:
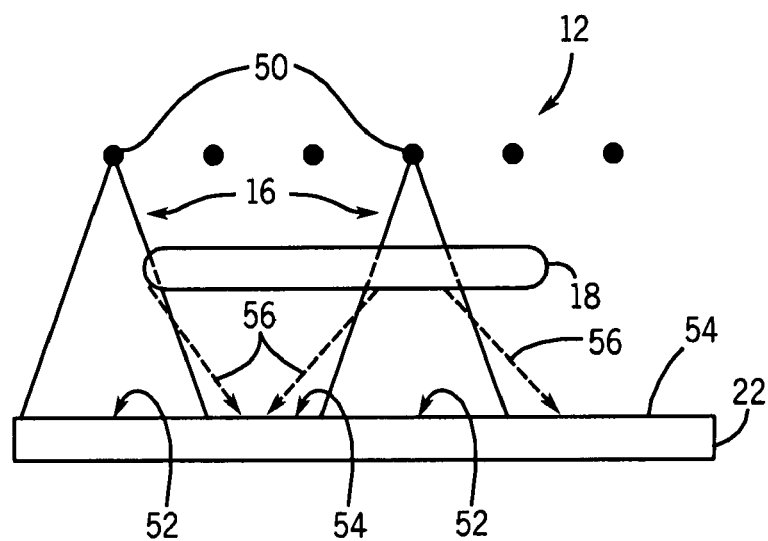
FIG. 2 depicts the activation of a subset of X-ray emission points positioned along the z-axis of an exemplary CT imaging system in accordance with one aspect of the present technique.
Figure 3:
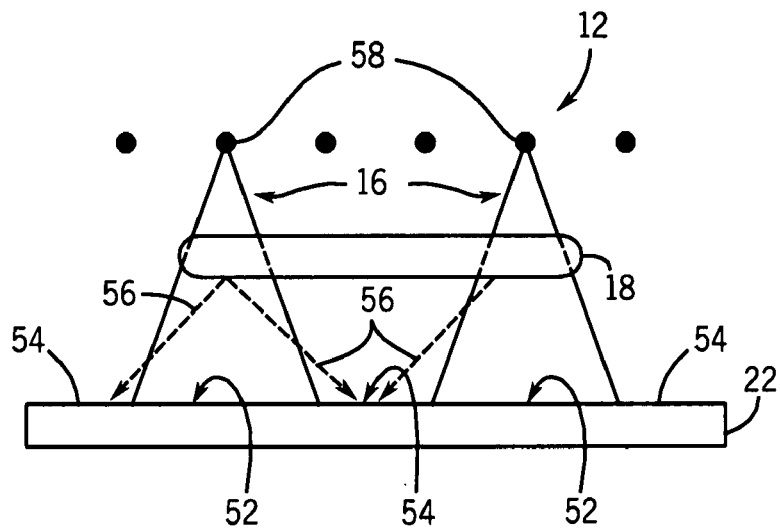
FIG. 3 depicts the activation of a second subset of X-ray emission points positioned along the z-axis of an exemplary CT imaging system in accordance with one aspect of the present technique.
Figure 4:
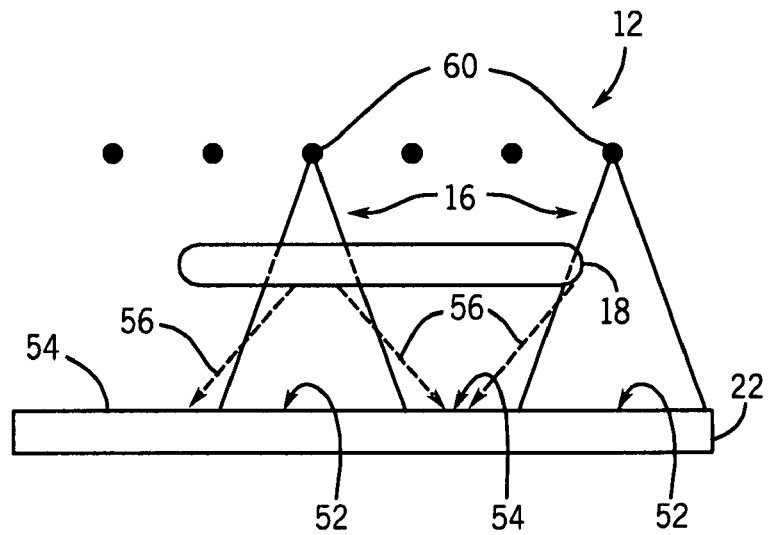
FIG. 4 depicts the activation of a third subset of X-ray sources positioned along the z-axis of an exemplary CT imaging system in accordance with one aspect of the present technique.

FIGS. 2-4 illustrate the sequential activation of emission point subsets. In the example embodiment in FIGS. 2-4, there are six emission points and three subsets, each subset consisting of two emission points. Although shown as such, any configuration of two or more emission points can be operated in the manner described herein. Beginning with FIG. 2, the first sequence of emission point subset activation is shown, including the X-ray source 12 comprising six emission points. The emission points may be collectively enclosed within the same vacuum enclosure or separately contained within separate vacuum vessels. The active emission points 50 represent the first subset of emission points and are the only emission points emitting radiation in the first sequence. The radiation beams 16 pass through the patient or object 18 to be scanned. As discussed above, the majority of the radiation beams impact the detector array 22 at the primary radiation exposure area 52, but there are areas 54 of the detector array not within the path of the primary radiation beams 16. Some scattered radiation 56 from the radiation beams 16 impacts the areas 54 of the detector array 22, and the incidence of X-rays on the areas 54 is then used to estimate scatter of the radiation beams 16.

Turning now to FIG. 3, the second activation sequence is shown. The active emission points 58 represent the second subset of emission points. The beams of radiation 16 from the active emission points 58 pass through the patient or object 18 and impact the detector array 22. The area 54 on the detector array represents an area not within the path of the primary radiation beams 16, and the areas 54 receive only the scattered radiation 56 from the radiation beams 16. Signals acquired at the areas 54 are used to estimate scatter during the second activation of the sequence.

Referring now to FIG. 4, the active emission points 60 represent the third and final subset of emission points in the example. The active emission points 60 emit beams of radiation 16, which pass through the patient or object 18 and impact the detector array 22. As all three subsets have now been activated, the entire axial volume has been illuminated by beams of radiation. As in the preceding examples, the areas 54 on the detector array represent areas not within the path of the primary radiation beams 16 that receive only the scattered radiation 56 from the radiation beams 16. The incidence of X-rays on the areas 54 is then used to estimate scatter during the third activation of the sequence.

Figure 5:
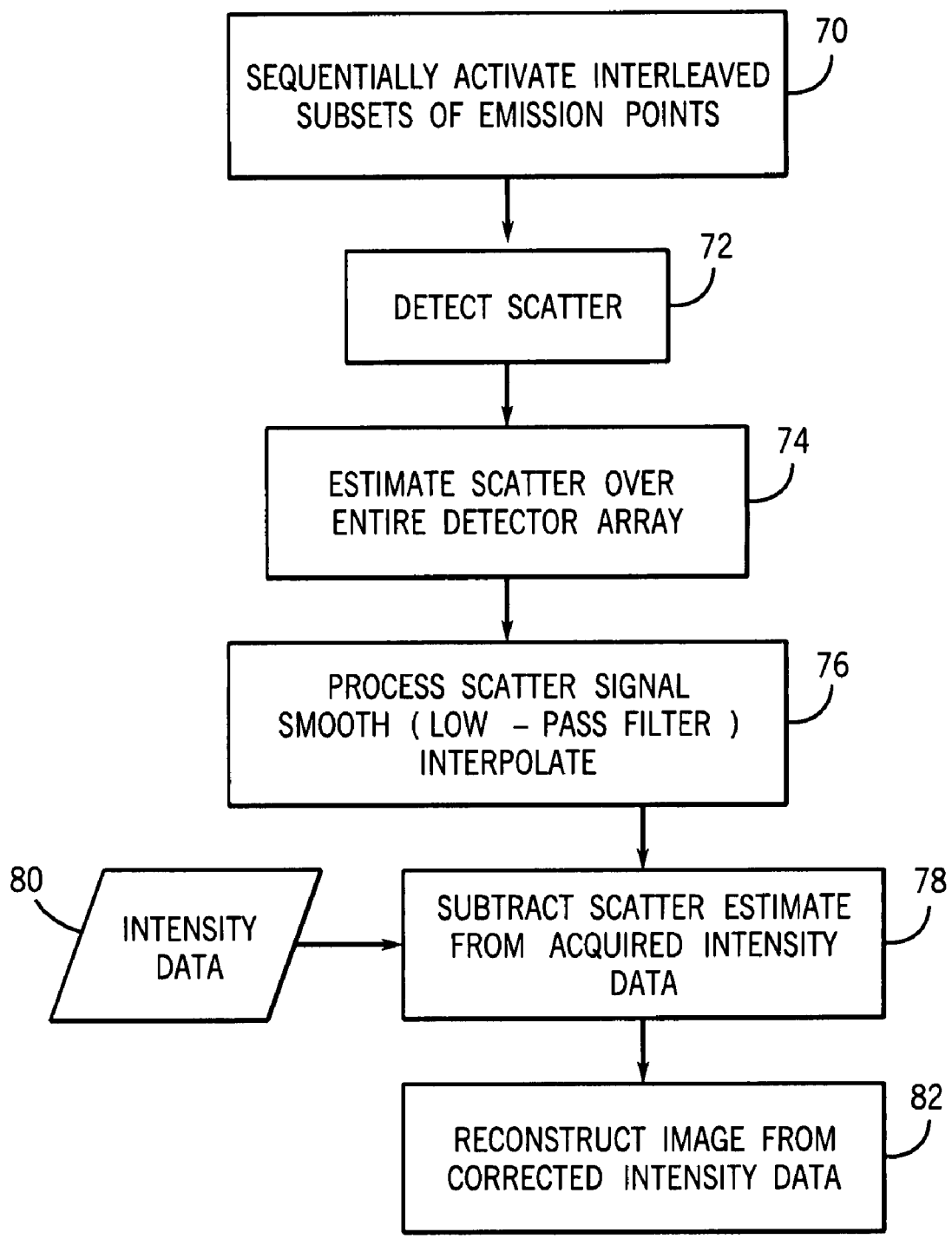
FIG. 5 is a flowchart depicting exemplary actions for processing images in accordance with the present technique for estimating and reducing scatter.

In FIG. 5 exemplary acts for reducing the effects of X-ray scatter using the system described in FIG. 1 are depicted. The acts described by the flowchart in FIG. 5 may be performed in any configuration of the system described above, so that the scatter estimation may be performed for any number of emission points, subsets, or any combination thereof. In the depicted example an interleaved subset of one or more emission points is sequentially activated (block 70) as described in FIGS. 2-4. While the subsets of emission points are activated in sequence, scatter is detected (block 72) and estimated (block 74) for the entire detector array based on the signal strength seen at the respective areas 54 outside the path of the primary radiation beams 16 during each activation sequence. The scatter may be processed (block 76) by smoothing the scatter to remove noise, such as with a low-pass filter or other filtering technique. In one implementation the scatter signal is interpolated to provide a scatter estimate across the entire detector on a view-by-view basis. The scatter estimate is subtracted (block 78) from the measured intensity data (block 80). A final image is reconstructed (block 82) from the corrected intensity data. The intensity data may be processed into projection data before reconstruction into a final image. Since the characteristics of scatter do not vary drastically within projection data acquired at adjacent angular positions of the gantry for CT imaging, it may be possible to estimate scatter for every other view position or every third view position, etc., and interpolate the scatter signal to reduce the computational complexity of the scatter correction technique. Alternately, the scatter can be incorporated into a forward model for an iterative reconstruction algorithm.

In view of the techniques described above, scatter can be reduced in radiographic images without the use of hardware collimators associated with the detector array 18, thereby reducing mechanical complexity and cost. Alternatively, scatter can be further reduced in radiographic imaging from system configurations that incorporate hardware collimators alone with detector array 18. Further, other methods of scatter estimation or reduction for use with wide-cone CT systems, such as narrowing the cone beam or providing two-dimensional scatter grids, may be unnecessary. Collimation, anti-scatter grids, or other methods for reducing scatter or improving image quality can be combined with the techniques above, and such methods may be simplified to reflect the efficacy of the present technique, such as by collimating the radiation beams in only one dimension.

While only certain features of the invention have been illustrated and described herein, many modifications and changes will occur to those skilled in the art. For example, though the present discussion has been in the context of medical imaging using radiographic systems, one of ordinary skill in the art will appreciate that the present techniques are equally applicable to radiographic and tomosynthesis systems and also to non-medical imaging applications employing X-ray sources that may move relative to the detection apparatus. For example, the present techniques may also be applied to non-invasive and/or non-destructive imaging techniques used for security and quality control applications in the fields of baggage and package screening, manufacturing quality control, security screening and so forth. Additionally, although the techniques and X-ray source topologies described herein consider multiple spots along the z-axis, the techniques can equally be applied to multiple spots distributed within the axial plane, as long as scatter estimates can be made at a finite number of sample positions on the detector. It is, therefore, to be understood that the appended claims are intended to cover all such modifications and changes as fall within the true spirit of the invention.

The invention claimed is:

1. A method for correcting scatter in an image, comprising:
   sequentially emitting radiation from a subset of one or more radiation sources toward a detector array;
   measuring radiation on areas of the detector array that are not exposed to the emitted primary radiation at the time of measurement; and
   estimating a scatter signal from the measured radiation.

2. The method of claim 1, comprising smoothing the estimated scatter signal to remove noise.

3. The method of claim 1, wherein estimating a scatter signal comprises estimating scatter for each cell of the detector.

4. The method of claim 1, comprising subtracting the scatter estimate from a set of measured intensity data acquired at areas of the detector that are exposed to the emitted primary radiation to generate a set of corrected intensity data.

5. The method of claim 4, comprising reconstructing an image from the set of corrected intensity data.

6. The method of claim 1, comprising collimating the sequentially emitted primary radiation.

7. The method of claim 1, wherein the at least one radiation source is arranged along the z-axis of an imaging scanner.

8. The method of claim 1, wherein the at least one radiation source is arranged along the axial plane of an imaging scanner.

9. The method of claim 1, wherein the subset consists of the number of radiation sources divided by an integer greater than or equal to two or less than or equal to the number of radiation sources.

10. The method of claim 1, comprising sequentially emitting radiation from a subset of at least two and no more than fifteen radiation sources.

11. An imaging system, comprising:
    one or more radiation sources along the z-axis, each radiation source configured to emit a beam of radiation;
    a detector array comprising a plurality of detector elements, wherein each detector element may generate one or more signals in response to the respective beams of radiation;
    a system controller configured to control the radiation sources, including activating subsets of the radiation sources sequentially;
    the system controller further configured to acquire the one or more signals from the plurality of detector elements, including detector elements not exposed to the beams of primary radiation at the time of acquisition; and
    a computer system configured to estimate scatter over the entire detector array.

12. The system of claim 11, wherein the computer system is configured to estimate scatter for each detector element.

13. The system of claim 12, wherein the computer system is configured to subtract the scatter estimate from the signals generated by the detectors in response to the respective beams of radiation.

14. The system of claim 11, wherein the computer system is configured to receive the one or more signals and to process the one or more signals to generate one or more images.

15. The system of claim 11, comprising an operator workstation configured to display the one or more images.

16. The system of claim 11, comprising an anti-scatter grid.

17. One or more tangible, machine readable media, comprising code executable to perform the acts of:
    sequentially emitting radiation from a subset of at least one or more radiation sources toward a detector array;
    measuring radiation on areas of the detector array that are not exposed to the emitted primary radiation at the time of measurement; and
    estimating scatter from the measured radiation.

18. The one or more tangible, machine readable media of claim 17, comprising smoothing the scatter signal to remove noise in the scatter estimate.

19. The one or more tangible, machine readable media of claim 17, comprising estimating scatter for a each cell of the detector.

20. The one or more tangible, machine readable media of claim 17, comprising subtracting the scatter estimate from a set of measured intensity data acquired at areas of the detector that are exposed to the emitted primary radiation to generate a set of corrected intensity data.

21. The one or more tangible, machine readable media of claim 20, comprising reconstructing an image from the set of corrected intensity data.

22. The one or more tangible, machine readable media of claim 17, comprising collimating the sequentially emitted primary radiation.

23. The one or more tangible, machine readable media of claim 17, wherein the at least two radiation sources are arranged along the z-axis of an imaging scanner.

24. The one or more tangible, machine readable media of claim 17, wherein the subset consists of the number of radiation sources divided by an integer greater than or equal to two or less than or equal to the number of radiation sources.

25. The one or more tangible, machine readable media of claim 17, comprising sequentially emitting radiation from a subset of at least two or no more than fifteen radiation sources.

* * * * *